(12) United States Patent
Powers

(10) Patent No.: US 6,329,822 B1
(45) Date of Patent: Dec. 11, 2001

(54) PERIODIC AUTOMATIC SELF-TEST SYSTEM AND METHODOLOGY

(76) Inventor: Daniel J. Powers, 2145 Squak Mountain SW., Issaquah, WA (US) 98027

( * ) Notice: Subject to any disclaimer, the term of this patent is extended or adjusted under 35 U.S.C. 154(b) by 0 days.

(21) Appl. No.: 09/502,804

(22) Filed: Feb. 11, 2000

(51) Int. Cl.$^7$ .................................................. G01N 27/416
(52) U.S. Cl. ......................................................... 324/426
(58) Field of Search .................................. 324/426, 427; 602/5; 702/63

(56) References Cited

U.S. PATENT DOCUMENTS

| | | | |
|---|---|---|---|
| 4,080,558 | 3/1978 | Sullivan | 320/39 |
| 5,235,979 | 8/1993 | Adams | 607/5 |
| 5,372,605 | 12/1994 | Adams et al. | 607/5 |
| 5,483,165 | 1/1996 | Cameron et al. | 324/427 |
| 5,625,291 | 4/1997 | Brink et al. | 324/427 |
| 5,640,078 | 6/1997 | Kou et al. | 320/15 |
| 5,721,482 | 2/1998 | Benvegar et al. | 320/43 |
| 5,800,460 | 9/1998 | Powers et al. | 607/5 |
| 5,868,794 | 2/1999 | Barkley et al. | 607/5 |
| 5,879,374 | 3/1999 | Powers et al. | 607/5 |
| 5,889,388 | 3/1999 | Cameron et al. | 320/166 |
| 5,899,925 | 5/1999 | Ochs et al. | 607/5 |
| 5,929,601 | 7/1999 | Kaib et al. | 320/113 |
| 5,929,764 | 7/1999 | Brink et al. | 340/636 |

OTHER PUBLICATIONS

"DS2434 Battery Identification Chip," Dallas Semiconductor Corporation pp. 1–20, Nov. 20, 1999.
"Programming DS243x Battery Identification Chips," Tech. Brief No. 5, Dallas Semiconductor Corporation, pp. 1–9, Oct. 31, 1999.

*Primary Examiner*—Gregory J. Toatley, Jr.

(57) ABSTRACT

An electrotherapy device such as a portable defibrillator that performs one or more periodic automatic self-tests, the periodicity of which is a function of one or more characteristics of an installed power module which may be, for example, a rechargeable battery pack, non-rechargeable battery pack or AC power pack. A self-test protocol of one or more self-tests can be modified to accommodate the characteristics of one or more installed power modules, allowing the device to be equipped to operate with any power module appropriate for the device and its intended use model. The periodicity of the self-tests may be based on characteristics of an installed power module such as battery capacity, battery chemistry, rechargeability, and anticipated use model.

28 Claims, 7 Drawing Sheets

FIG. 5

| BYTE # | CHARACTERISTICS | BYTE VALUES (MSB) 7 | 6 | 5 | 4 | 3 | 2 | 1 | (LSB) 0 | OPTIONS/DESCRIPTIONS |
|---|---|---|---|---|---|---|---|---|---|---|
| 502A | 510 DEFAULT SELF-TEST INTERVAL | 0 | 0 | | | | | | | ONCE EVERY 28 DAYS |
| | | 0 | 1 | | | | | | | ONCE EVERY 14 DAYS |
| | | 1 | 0 | | | | | | | ONCE EVERY 7 DAYS |
| | | 1 | 1 | | | | | | | ONCE EVERY 3 DAYS |
| | 512 LOW-ENERGY SELF-TEST INTERVAL | | | 0 | 0 | | | | | ONCE EVERY 28 DAYS |
| | | | | 0 | 1 | | | | | ONCE EVERY 14 DAYS |
| | | | | 1 | 0 | | | | | ONCE EVERY 7 DAYS |
| | | | | 1 | 1 | | | | | ONCE EVERY 3 DAYS |
| | 514 ACCUMULATED SELF-TEST DELTA | | | | | X | X (UNSIGNED) | X | X | LSB = 128 COULOMBS |
| 502B | 516 COULOMB COUNTER ACCUMULATOR | X | X | X | X | X (UNSIGNED) | X | X | X | LSB = 128 COULOMBS. INCREMENT IN RUNTIME BASED ON BATTERY CURRENT. ESTIMATE USAGE FOR SELF-TESTS, NON-RUNTIME OPERATIONS. |
| 502C | 518 LOW ENERGY CONDITION | X | X | X | X | X (UNSIGNED) | X | X | X | LSB = 128 COULOMBS. THE NUMBER OF ACCUMULATED COULOMBS THAT REPRESENTS A LOW BATTERY CONDITION. |

204 DATA STORAGE DEVICE

PERIODIC AUTOMATIC SELF-TEST SYSTEM AND METHODOLOGY

RELATED APPLICATIONS

The following applications are related to the present application and are incorporated by reference herein and elsewhere in this application: U.S. Pat. No. 5,607,454 to Cameron et al., entitled "Electrotherapy Method and Apparatus;" U.S. Pat. No. 5,800,460 to Powers et al., entitled "Method For Performing Self-Test in a Defibrillator;" U.S. Pat. No. 5,879,374 to Powers et al., entitled "External Defibrillator With Automatic Self-Testing Prior to Use;" U.S. patent application Ser. No. 09/191,685, entitled "Battery Pack Chemistry Detection and Identification System and Method," filed Nov. 13, 1998; U.S. patent application Ser. No. 09/192,116, entitled "System and Method for Detecting Performance Components of a Battery Pack," filed Nov. 13, 1998; U.S. Pat. No. 5,483,165 to Cameron et al., entitled "Battery System and method For Determining A Battery Condition;" and U.S. patent application Ser. No. 09/184,485 filed Nov. 2, 1998 under attorney docket no. 10980507-1, entitled "A Conforming Intelligent Battery Label."

BACKGROUND OF THE INVENTION

1. Field of the Invention

The present invention relates generally to determining the rate of performing periodic automatic self-tests in such a device.

2. Related Art

Electrotherapy devices are used to provide electrical shocks to treat patients for a variety of heart arrhythmias. For example, external defibrillators typically provide relatively high-energy shocks to a patient as compared to implantable defibrillators, usually through electrodes attached to the patient's torso. External defibrillators are used to convert ventricular fibrillation or shockable tachycardia to a normal sinus rhythm. Similarly, external cardioverters can be used to provide shocks to convert atrial fibrillation to a more normal heart rhythm.

Conventional external defibrillators have been used primarily in hospitals and other medical care facilities. In such environments, the frequency with which a particular defibrillator is operated, referred to as the use model, is significant, perhaps on the order of several times per week. Periodic tests for such defibrillators typically include a battery level test and a functional test in which the defibrillator is connected to a test load and discharged. These self-tests are usually performed daily or once per shift in accordance with manufacturer recommendations. Other tests, such as recalibration of internal circuit components by a biomedical technician, are performed less often, on the order of twice per year, which is also typically specified by the manufacturer. Each of these maintenance tests for conventional defibrillators have traditionally been initiated and performed by human operators, although more recently automatic invocation and execution of self-tests are becoming more commonplace.

While these external defibrillators have been known for years, they have generally been large and expensive making them unsuitable for use outside of a medical care facility. More recently, portable external defibrillators for use by first responders have been developed. Portable defibrillators allow medical care to be provided to a patient at the patient's location considerably earlier than preceding defibrillators, increasing the likelihood of survival.

Portable defibrillators typically use a portable energy source to operate in the anticipated mobile environment. Several defibrillator and after-market manufacturers have produced battery packs for such defibrillators. These battery packs, while often having a standard mechanical and electrical interface, are available with different chemistries, such as lead acid, nickel cadmium, lithium ion and the like. These battery packs have traditionally been rechargeable due to the anticipated high frequency use model.

With recent advances in technology, portable defibrillators have become more automated, allowing even a minimally trained operator to use such devices to aid a heart attack victim in the critical first few minutes subsequent to the onset of sudden cardiac arrest. Such portable defibrillators, referred to as automatic or semi-automatic external defibrillators (generally, AED's), may be stored in an accessible location at a business, home, aircraft or the like. Due to the increased diligence required to properly maintain rechargeable battery packs, some recently developed portable defibrillators have been configured to receive a non-rechargeable battery pack. This is more common in recent history due to advances in battery technology that have allowed for the development of long life, high capacity non-rechargeable battery packs.

One particular problem that arises using currently available portable defibrillators is that occasionally it may be necessary or desired to operate the device in accordance with a use model different than that for which the defibrillator was originally designed. One characteristic of traditional defibrillators that prevents such a change in operation is the implementation of a self-test protocol that verifies the reliability of the defibrillator, including the installed battery pack. The self-test protocol is traditionally established when the defibrillator is manufactured in anticipation that the defibrillator will be used with a particular battery pack. Unfortunately, the defibrillator is required to thereafter restrict the battery packs that it is receives to only the particular type of battery pack that can support and be verified by the implemented self-test protocol. This in turn prevents the defibrillator from being operated in accordance with a use model other than that which the defibrillator was originally designed due to limitations associated with the acceptable type of battery pack.

What is needed, therefore, is a method and apparatus for insuring the reliability and availability of a device such as a portable defibrillator without restricting or otherwise limiting the use model of the device.

SUMMARY OF THE INVENTION

The present invention is directed to the performance of one or more periodic automatic self-tests of a powered device, the periodicity of which is a function of one or more characteristics of an installed power module, such as a battery pack or AC power pack. Advantageously, a desired device reliability can be achieved by adjusting the periodicity of the self-tests to optimally verify a particular installed power module. As a result, the device is not required to restrict the type of power module that it receives to only the type that can support and be verified by an implemented self-test protocol. Rather, the self-test protocol may be modified to accommodate the characteristics of an installed power module, allowing the device to be equipped to operate with any power module appropriate for use with that device and the intended use model. This allows the device to be operated with different types of power modules and, therefore, in accordance with different use models.

A number of aspects of the invention are summarized below, along with different embodiments that may be implemented for each of the summarized aspects. It should be understood that the summarized embodiments are not necessarily inclusive or exclusive of each other and may be combined in any manner in connection with the same or different aspects that is non-conflicting and otherwise possible. These disclosed aspects of the invention, which are directed primarily to systems, methods, data and techniques related to the performance of self-tests in powered devices, are exemplary aspects only and are also to be considered non-limiting.

In one aspect of the invention, a method for performing automatically a self-test in a powered device is disclosed. The method includes the steps of: (a) determining a periodicity at which the self-test is to be performed based on one or more characteristics of an installed power module; and (b) performing the self-test at the determined periodicity. The method may also include a step (c) prior to step (a), storing one or more variables in a data storage device in the power module, wherein the variables are indicative of the characteristics of the power module considered in step (a). In one embodiment, the determining step comprises the steps of (a)(i) monitoring the characteristics from the installed power module; and (a)(ii) determining the periodicity for the self-test based on monitored characteristics. In one embodiment wherein the power module is a battery pack, the monitored characteristics may include battery characteristics such as battery chemistry, rechargeability, current battery capacity, self-test periodicity and projected frequency of use.

In another aspect of the invention, a test interval determinator is disclosed. The test interval determinator determines a periodicity at which a periodic automatic self-test of a powered device is to be performed. The determinator is configured to receive at least one characteristic of a power module installed in the device, and to generate a period at which the self-test is to be performed, wherein the self-test period is a function of the at least one characteristic of the power module. The power module may be, for example, a battery pack or an AC power pack.

In a further aspect of the invention, an electrotherapy device that performs one or more periodic automatic self-tests is disclosed. The period of each self-test is determined based on one or more characteristics of an installed power module.

In a still further aspect of the invention, a system for determining a periodicity at which power-consuming self-tests are performed in a device is disclosed. The system includes a battery pack and a self-test module. The battery pack includes an indicator of one or more characteristics of the battery pack. The self-test module performs one or more automatic self-tests, each with a periodicity that is a function of one or more of the indicated battery characteristic(s). The battery characteristic(s) may be, for example, battery chemistry, rechargeability, current battery capacity, self-test periodicity or projected frequency of use. The self-test module may be implemented in a medical device adapted to receive the battery pack. One example of such a device is a defibrillator. The indicator of the battery characteristics may be a data storage device integrated in the battery pack. The data storage device has stored therein one or more variables individually or collectively representative of the indicated battery characteristic(s).

In a still further aspect of the invention, a system for determining a periodicity at which power-consuming self-tests are performed in a device is disclosed. The system includes a power module and a self-test module. The power module includes an indicator of one or more characteristics of the power module. The self-test module performs one or more automatic self-tests, each with a periodicity that is a function of one or more of the indicated power module characteristic(s). The power module characteristic(s) may be, for example, battery chemistry, rechargeability, current battery capacity, self-test periodicity or projected frequency of use. The self-test module may be implemented in a medical device adapted to receive the power module. One example of such a device is a defibrillator. The indicator of the power module characteristics may be a data storage device integrated in the power module. The data storage device has stored therein one or more variables individually or collectively representative of the indicated power module characteristic(s).

In another aspect of the invention, a power module for installation in a powered device that performs automatic self tests is disclosed. The power module includes an apparatus that provides the device with an indication of one or more characteristics of the power module for use in determining the periodicity at which the device performs each self-test. The power module may be a rechargeable battery pack, a non-rechargeable battery pack or an AC power pack.

In a further aspect of the invention, a defibrillator that performs a self-test at a periodicity based on a use model of the defibrillator is disclosed. The use model is derived from an installed power module. In another embodiment, the use module is derived from an identification of the power module. For example, in one embodiment, the use model is derived from a chemistry of a battery pack. In yet another embodiment, the self-test periodicity is based on capacity of the battery pack. Of course, it will be appreciated by those of skill in the art that other parameters may be used as well. Other parameters include but are not limited to voltage, power delivery capability, energy, etc. Preferably, the periodicity increases as the capacity decreases. The self-test may include fully charging and discharging an energy delivery system of the defibrillator.

Various embodiments of the present invention provide certain advantages and overcome certain drawbacks of conventional self-test techniques. Not all embodiments of the invention share the same advantages and those that do may not share them under all circumstances. This being said, the present invention provides numerous advantages including the noted advantage of allowing for the modification of a self-test protocol to accommodate an installed battery pack, thereby allowing the device to be operated with any battery pack appropriate for the device and anticipated use model. These and other features and advantages of the present invention as well as the structure and operation of various embodiments of the present invention are described in detail below with reference to the accompanying drawings.

BRIEF DESCRIPTION OF THE DRAWINGS

The above and further advantages of the invention will be more clearly appreciated from the following detailed description when taken in conjunction with the accompanying drawings, in which like reference numerals indicate like structures or method steps, in which the left-most one or two numerals of a reference numeral indicate the number of the figure in which the referenced element first appears, and in which:

FIG. 5 is an illustration of exemplary characteristics that may be stored in the data storage device illustrated in FIG. 2 in accordance with one embodiment of the present invention.

DETAILED DESCRIPTION

The present invention is directed to a system and associated methodologies for performing a periodic automatic self-test of a device, the periodicity of which is a function of one or more characteristics of an installed power module. The periodicity of the self-test can be adjusted to accommodate the characteristics of an installed power module, allowing the device to operate with any type of power module appropriate for the device and anticipated use model. The power module may be, for example, any type of rechargeable or non-rechargeable battery pack, AC power pack and the like.

Figure 1:
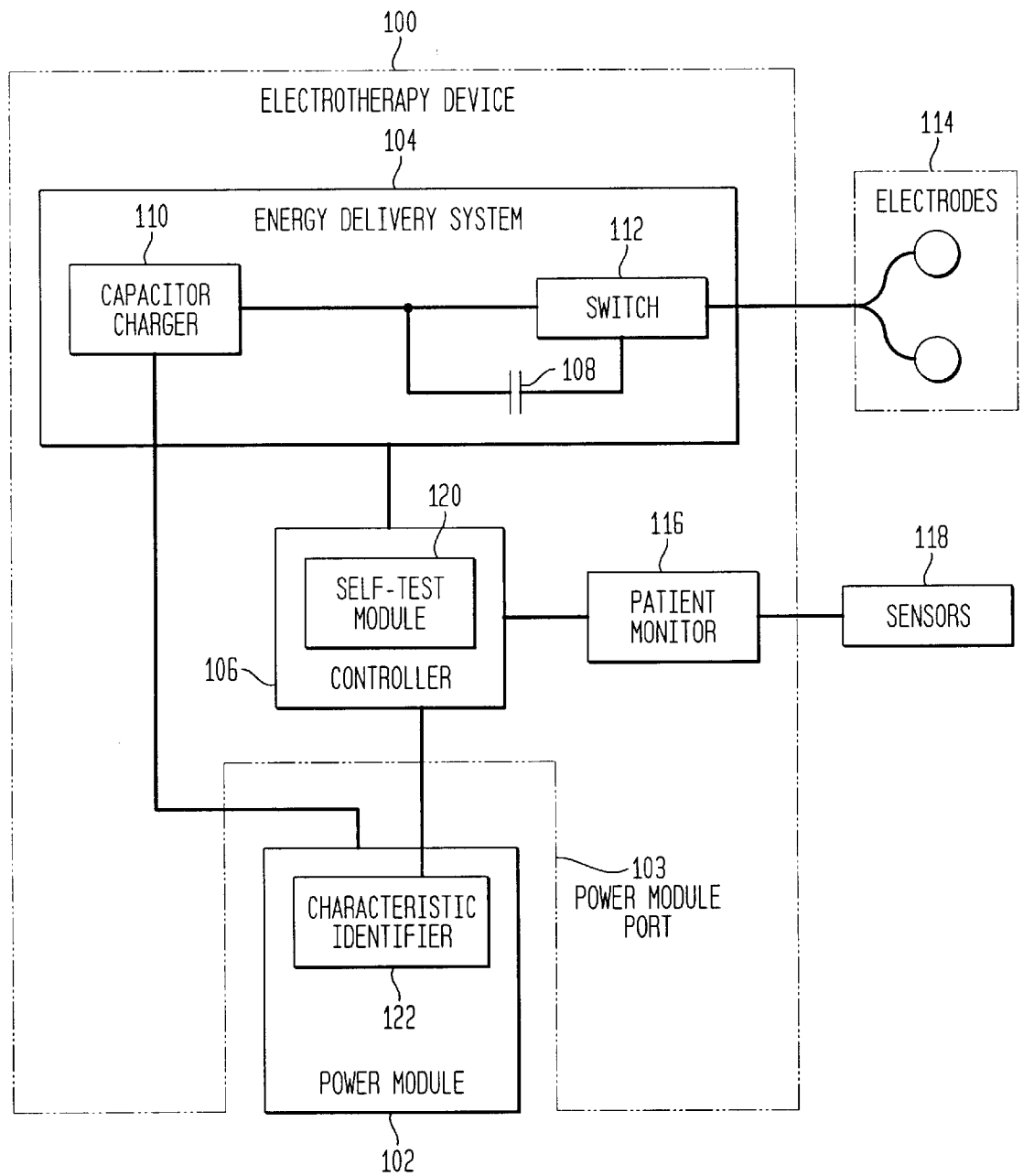
FIG. 1 is a simplified block diagram of an exemplary electrotherapy device implementing a periodic automatic self-test system in accordance with one embodiment of the present invention.

Aspects and embodiments of the present invention will be described herein with reference to a particular type of powered device commonly known as an electrotherapy device. FIG. 1 is a simplified block diagram of an exemplary electrotherapy device 100. Electrotherapy device 100 may include the necessary components to defibrillate, cardiovert or pace a patient, or to perform any combination of such operations. It should be appreciated that since such electrotherapy devices are well known in the art, the components described herein and illustrated in FIG. 1 are exemplary only. In the following description it is envisioned that electrotherapy device 100 is a portable defibrillator such as the many models of portable defibrillators available from Heartstream, Inc., Seattle, Wash. and Agilent Technologies, Palo Alto, Calif.

Components of electrotherapy device 100 operate under the control of a controller 106. Controller 106 may be embodied in a microprocessor, gate array, ASIC, or other control logic architecture, as well as any combination thereof. Preferably, controller 106 is implemented in software code that is executed on a commercially available microprocessor. Generally, such software code is stored in a memory device (not shown) accessible by the microprocessor.

Electrotherapy device 100 includes an energy delivery system 104 that delivers energy to a patient (not shown). Energy delivery system 104 is connected to electrodes 114 and includes generally a capacitor or capacitor bank 108, a capacitor charger 110 and a switching mechanism 112. In response to controller 106, energy delivery system 104 delivers an electric shock from capacitor 108 to electrodes 114 that are placed on the patient's chest.

Patient monitor 116 monitors the patient's heart rhythm and determines whether the monitored rhythm is shockable. Patient monitor 116 receives information from sensors 118, which may be integrated in electrodes 114, as physically separate devices or a combination thereof. Patient monitor 116 communicates a shock decision to controller 106. Energy delivery system 104 then delivers a therapeutic energy pulse to the patient via electrodes 114.

These and other components of electrotherapy device 100 are well known in the art. Electrotherapy devices suitable for implementing the present invention may include the same or similar device components now or later developed. Further, these components serve as an example of the components that are subject to the automated self-tests performed in accordance with the present invention. The above and other device components not specifically described in this application may be included and configured to operate in the manner described in U.S. Pat. No. 5,607,454 to Cameron et al., entitled "Electrotherapy Method and Apparatus," the disclosure of which is incorporated herein by reference in its entirety.

In accordance with the exemplary aspects of the present invention, device 100 includes a self-test module 120 that performs one or more periodic automatic self-tests with a periodicity that is determined based on one or more characteristics of an installed power module such as a battery pack or AC power pack. In this illustrative embodiment, electrotherapy device 100 includes a power module receptacle 103 in which a power module pack 102 is installed. A power module characteristic identifier 122 is preferably integrated into power module 102 and is constructed and arranged to communicate with self-test module 120 in electrotherapy device 100. Characteristic identifier 122 and self-test module 120 are collectively referred to herein as a power module-responsive automatic self-test system.

Although a single power module 102 and port 103 are illustrated in FIG. 1, it should become apparent from the present disclosure that the present invention may be implemented in any number or combination of concurrently installed power modules. In systems that incorporate more than one power module 102, a power module selector (not shown) may be implemented in electrotherapy device 100. Such a power module selector may determine which installed power module is to provide power to electrotherapy device 100 and which is to be connected to a battery charge circuit (also not shown).

Self-test module 120 performs, manages, invokes or otherwise controls ("performs" herein) one or more automatic self-tests on electrotherapy device 100, its systems, subsystems, modules, components and the like ("device components" herein) to verify the operational status of such device components. The periodicity or time interval between successive performances of each such self-test is determined in accordance with the present invention based on one or more characteristics of an installed power module. As will become apparent, the term "power module characteristic" is to be interpreted broadly to include any sensed or calculated physical, electrical or mechanical aspect of the power module, current or historical states or conditions, configuration, manufacturer, ownership, service and maintenance information, and any and all other related information. In addition, a power module characteristic may be an absolute or relative value. In one embodiment described below, the power module characteristics for a battery pack include, for example, battery capacity and the periodicity at which a self-test is to be performed during normal and low battery capacity conditions. In another embodiment, the same or other power module characteristic(s) are utilized to calculate the self-test periodicity.

It should be understood that the amount of power required to perform a self-test varies depending on the nature of the self-test. For example, a low-level circuit test typically consumes very little or no power. On the other hand, a high voltage calibration test consumes a large amount of power. Although managing the periodicity of self-tests that use relatively small amounts of power is within the scope of the present invention, management of such a self-test will likely do little to insure future device availability through the conservation of battery pack capacity.

In some of today's defibrillators a self-test protocol that includes more than one self-test is implemented. Such self-tests may be divided into categories according to power usage, with the categories of self-tests scheduled to take into account the power source or power module. Thus, when the power module is a battery pack, the self tests are performed so as to preserve the life of the installed battery pack, particularly when that battery pack is a non-rechargeable battery pack. For example, those self-tests that consume considerable power may be assigned to a category of self-tests that are performed less frequently than a category of self-tests that consume minimal power. Self-test module 120 may be configured to perform such multiple self-tests as described in U.S. Pat. No. 5,800,460 to Powers et al., entitled "Method For Performing Self-Test in a Defibrillator" and U.S. Pat. No. 5,879,374 also to Powers et al., entitled "External Defibrillator With Automatic Self-Testing Prior to Use," the disclosures of which are incorporated by reference herein in their entirety. However, in contrast to such techniques, aspects of the present invention may be used to determine and adjust the periodicity of such self-tests individually or by category based on one or more characteristics of an installed power module.

In the exemplary embodiment illustrated in FIG. 1, self-test module 120 is embodied as a separate operational unit, implemented as software code operating on controller 106. As should be apparent to those of ordinary skill in the art, self-test module 120 may be implemented in any well-known manner now or later developed. For example, self-test module 120 may be implemented as a separate, processor-based system, in hardware circuitry, ASICs, gate arrays and the like. In addition, self-test module 120 may also include components located within other electrotherapy device subsystems, such as within energy delivery system 104. In any event, self-test module 120 communicates with device components via communication channels (not shown) to control the self-tests and to gather information pertaining to the status of the tested device components. Self-test module 120 may also communicate indicator control signals to one or more status indicators (not shown) via communication channels.

Figure 2:
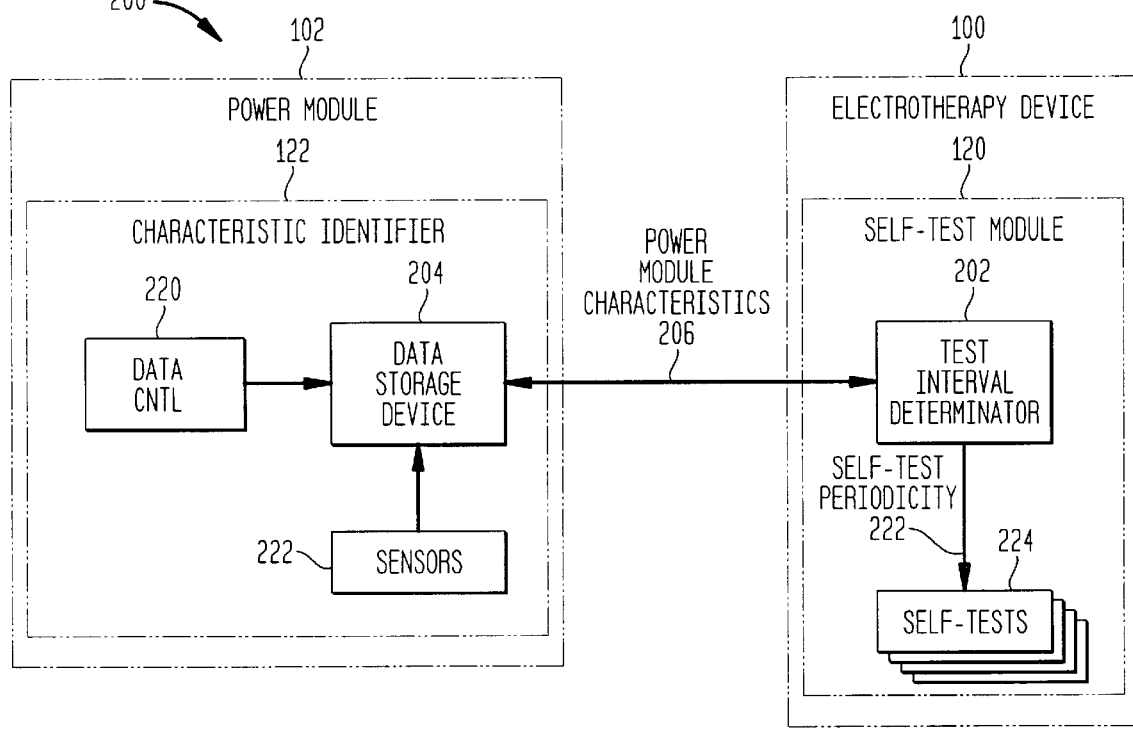
FIG. 2 is a functional block diagram of one embodiment of the present invention illustrating a power module characteristic identifier and responsive self-test module.

FIG. 2 is high-level functional block diagram of one embodiment of a self-test system of the present invention. A self-test system 200 includes the principal components of characteristic identifier 122 residing in power module 102 and self-test module 120 residing in electrotherapy device 100. A characteristic identifier 122 provides an identification of one or more power module characteristics 206 of power module 102. As will be described in detail below, characteristic identifier 122 may be implemented in a number of different embodiments each providing different features that represent characteristics 206. For example, data or electrical or physical features of characteristic identifier 122 can represent characteristics 206. This is described in greater detail below.

In the embodiments described herein, power module characteristics 206 are represented by data. Specifically, each characteristic 206 is represented by one or more variables stored as digital values in a data storage device 204. Storage device 204 may be any type of memory device now or later developed. In one embodiment described below, storage device 204 is implemented as non-volatile RAM (NVRAM) and/or static RAM (SRAM). Characteristic identifier 122 may include other elements such as data control 220 to provide the manufacturer with the capability to enter characteristics 206 into storage device 204, sensors 222 to detect characteristics 206 and store the values representing the sensed characteristics in storage device 204, etc.

Self-test module 120 performs periodically one or more automatic self-tests 224 on device components of electrotherapy device 100. Each self-test 224 is performed with a periodicity determined by test interval determinator 202 based on the provided power module characteristic(s). In this aspect of the invention, power module characteristics 206 are communicated via the installed power module 102. In accordance with one embodiment of the invention, storage device 204 is accessible to test interval determinator 202. Test interval determinator 202 in turn retrieves one or more of the stored characteristics 206 to determine the periodicity of one or more self-tests 224 in accordance with the present invention.

Test interval determinator 202 determines the periodicity of self-tests 224 based on any number of power module characteristics 206. In a simple implementation, a single characteristic 206 of self-test periodicity is considered. In such embodiments, the self-test periodicity may be stored as a single characteristic in storage device 204. In other embodiments, the determination is based on other characteristics in addition to or instead of self-test periodicity 208. Examples of the operations performed by test interval determinator 202 are provided below. It should become apparent from the present disclosure that characteristics 206 may be provided to self-test module 120 by installed power module 102 using other techniques, systems or methodologies. For example, in one alternative embodiment, characteristic identifier 122 is an electrical circuit. In such an embodiment, the characteristics may be represented by electrical features of the circuit such as the resistance provided by one or more resistors. The circuit can generate signals indicative of characteristics 206 or test interval determinator 202 can poll it in some well-known manner. In another embodiment, mechanical interface features may represent the characteristics 206. For example, one approach that may be used is disclosed in U.S. patent application Ser. No. 09/191,685, entitled "Battery Pack Chemistry Detection and Identification System and Method," and/or Ser. No. 09/192,116, entitled "System and Method for Detecting Performance Components of a Battery Pack," both of which were filed Nov. 13, 1998, the disclosures of which are incorporated by reference herein in their entirety. A still further alternative is to use a sense cell as described in U.S. Pat. No. 5,483,165 to Cameron et al., entitled "Battery System and Method For Determining A Battery Condition," the disclosure of which is incorporated by reference herein in its entirety. Other implementations of characteristic identifier 122 may be implemented, for example, as part of a smart battery label as described in U.S. patent application Ser. No. 09/184,485 filed Nov. 2, 1998 under attorney docket no. 10980507-1, entitled "A Conforming Intelligent Battery Label." The approach selected to communicate characteristics 206 to self-test module 120 ultimately depends upon the number of characteristics, the number of values each characteristic may assume, whether the characteristics are determined at time of manufacture (such as battery chemistry) or are determined dynamically (such as current battery capacity), the structure and function of power module 102 and device 100, etc., among other factors. The consideration of these and other factors is considered to be within the purview of those of ordinary skill in the art.

In certain embodiments described herein, test interval determinator 202 also transmits characteristics 206 to storage device 204, as indicated by the double-headed arrow 206 in FIG. 2. Such characteristics 206 of installed power module 102 may be calculated or otherwise determined by test interval determinator 202. Such characteristics 206 may then remain with power module 102 to be provided subsequently to other electrotherapy devices when installed therein.

Figure 3A:
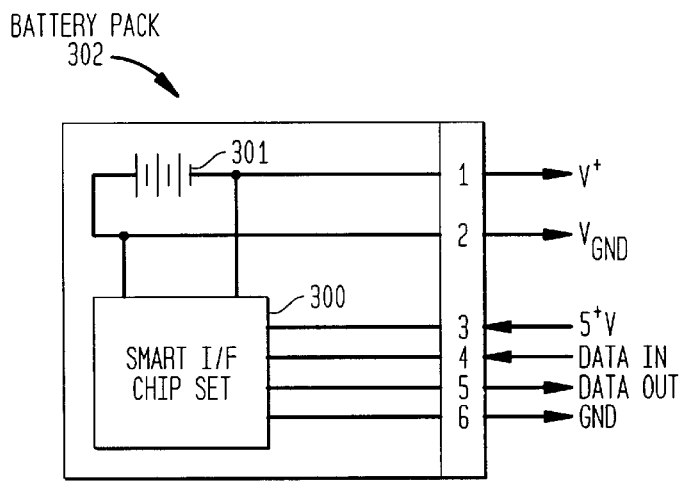
FIG. 3A is a block diagram of a battery pack in accordance with one embodiment of the present invention.

One embodiment of a battery pack 302 is illustrated in FIG. 3A. As shown therein, battery pack 302 includes one or more battery cells forming a battery 301 and a smart interface (I/F) chip set 300. Smart I/F chip set 300 provides the platform in which characteristic identifier 122 is implemented. Smart I/F chip set 300 may be connected to battery 301 as shown in FIG. 3A to measure the current battery capacity of battery 301. In addition, other components or features of battery pack 302 (not shown) may be implemented to measure, estimate, calculate or otherwise determine characteristics for storage in smart I/F chip set 300.

Battery pack 302 provides an interface that includes a voltage output (pin 1) and ground (pin 2) for battery 301, power for the smart interface (5 volts at pin 3) and data lines (receive at pin 4, transmit at pin 5 and ground at pin 6). Self-test module 120 communicates with battery pack 302 through a corresponding interface in electrotherapy device 100. It should be understood that battery pack 302 may include other components in addition to those illustrated in FIG. 3A. It should be further understood that storage device 204 may take on many other configurations implemented in any combination of software, hardware or firmware now or later developed. Accordingly, the embodiment illustrated in FIG. 3A is provided for illustrative purposes only.

Figure 3B:
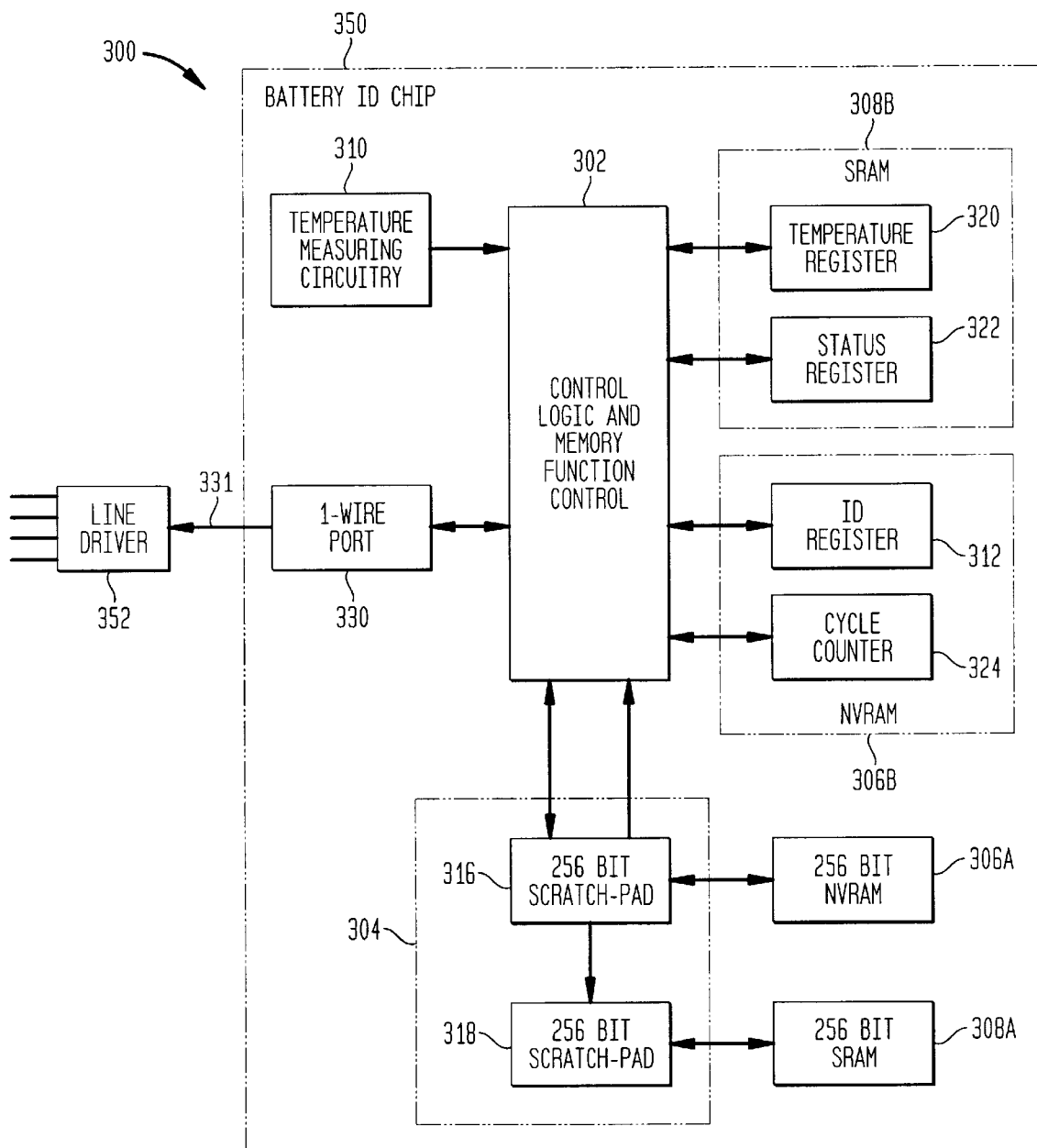
FIG. 3B is a block diagram of a characteristic identification chip with memory that may be installed in a battery pack in accordance with one embodiment of the present invention.

Referring to the particular implementation illustrated in FIG. 3A, smart interface chip set 300 may be implemented in any circuitry now or later developed. Smart interface chip set 300 provides a relevant characteristic information about the power module (here, battery pack 302) to the device. In one embodiment, smart interface 300 is implemented in the model DS243X family of battery identification chips available from Dallas Semiconductor Corporation, Dallas, Tex. In one particular embodiment illustrated in FIG. 3B a model DS2434 Battery Identification Chip 350 and a model DS2480 line driver 352 from Dallas Semiconductor Corporation, Dallas Tex., USA are integrated into battery pack 302 to perform the operations associated with characteristic identifier 122. The structure and operation of the DS2434 and DS2480 (as well as the other devices in the DS243X family) are described in detail in their respective data sheets, including the Dallas Semiconductor DS2434 Battery Identification Chip data sheet, the Dallas Semiconductor DS2480 Serial 1-Wire® Line Driver data sheet, as well as Dallas Semiconductor, "Tech Brief No. 5: Programming DS243X Battery Identification Chips" by Norbert Wank, all of which are available from Dallas Semiconductor Corporation, Dallas, Tex. (http://www.dalsemi.com/). Accordingly, the features of battery identification chip 350 are described only briefly herein.

The Dallas Semiconductor DS243X family of Battery Identification Chips provides a convenient method for storing characteristics 206 such as battery life, chemistry, charge/discharge characteristics, etc., in volatile or nonvolatile memory. In addition, a relatively simple method for tagging and identifying power module by manufacturer, battery chemistry or other identifying characteristics 206 is also provided. The exemplary DS2434 battery identification chip 350 provides a 1-Wire® interface port 330 ("1-Wire" is a registered trademark of Dallas Semiconductor Corporation, Dallas, Tex.). The use of such an interface 331 reduces the number of output connectors that need to be implemented on battery ID chip 350.

Battery identification chip 350 includes non-volatile Memory (NVRAM) 306A, 306B and static RAM (SRAM) 308A, 308B. As is well known, non-volatile memory devices continue to store information without applied power. On the other hand, static memory devices provide battery-backed storage of information. In this specific embodiment, there are four special-purpose registers included in battery identification chip 350. NVRAM 306B includes two registers 312, 324 to retain the ID number for the chip and the cycle count, respectively. SRAM 308B includes registers 320, 322 that contain the measured temperature value and status registers for the device.

Battery identification chip 350 includes a scratchpad memory 304 including two 256-bit memory regions 316, 318 for communicating with a 256-bit region of NVRAM 306A and a 256-bit region of SRAM 308A, respectively. Scratchpad memory regions 316 and 318 are used to insure data integrity when communicating over bus 331. Data is first written to the scratchpad where it can be read back. After the data has been verified, a "copy scratchpad" command will transfer the data to the SRAM 308 or NVRAM 306. This process insures data integrity when modifying the contents of the memory 306, 308.

Figure 4A:
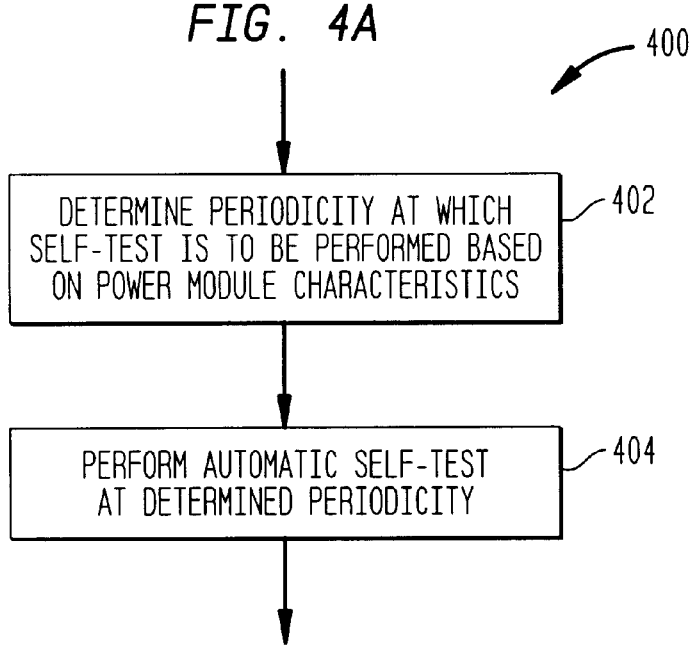
FIG. 4A is a high-level flow chart of the operations performed by the self-test module illustrated in FIG. 1 in accordance with one embodiment of the present invention.
Figure 4B:
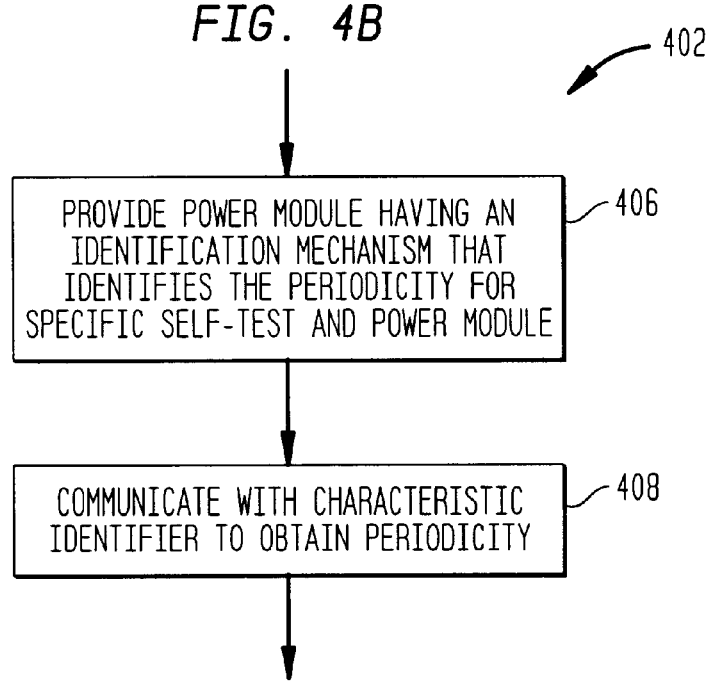
FIG. 4B is a flow chart of the operations performed in connection with one process illustrated in FIG. 4A in accordance with one embodiment of the invention.
Figure 4C:
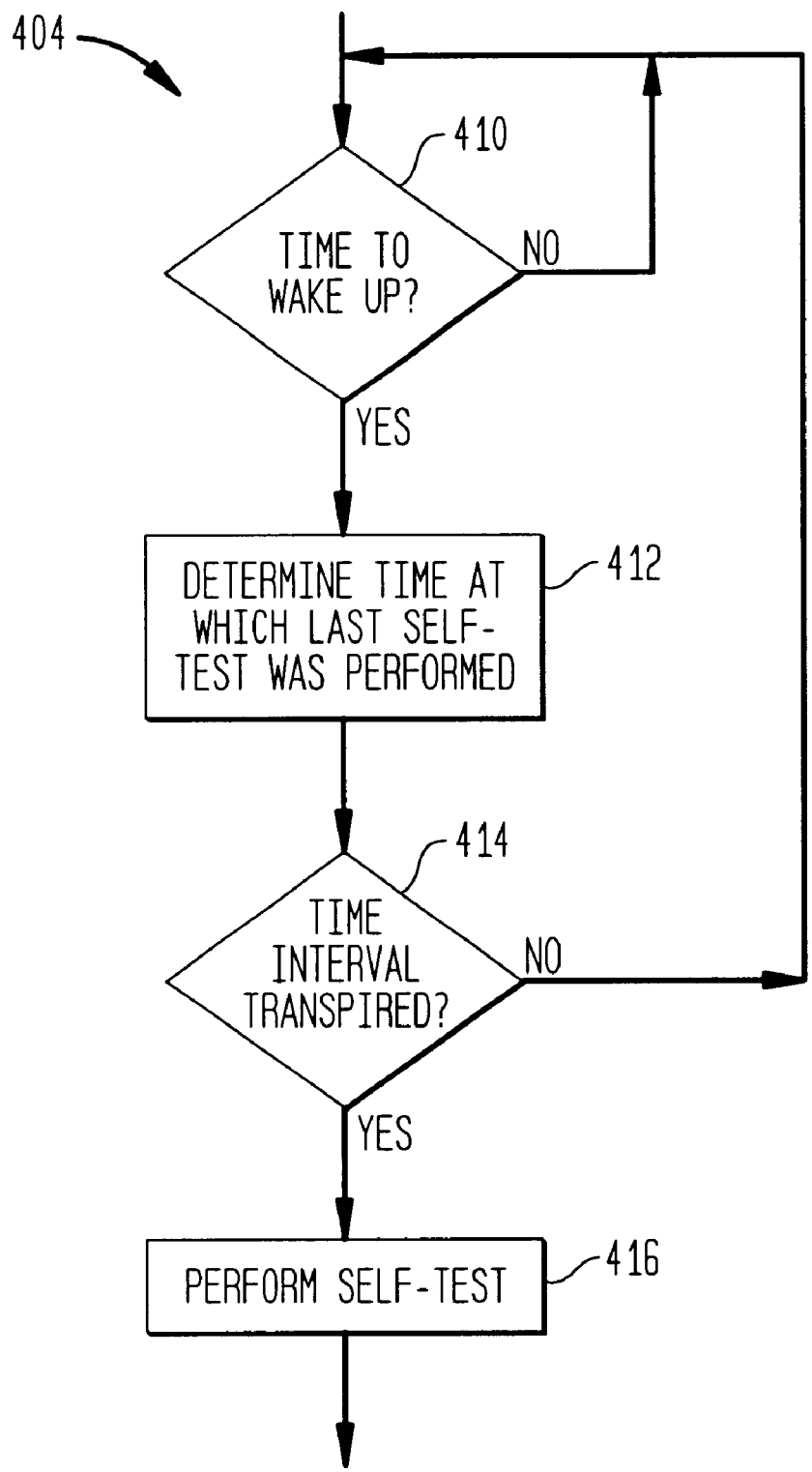
FIG. 4C is a flow chart of one embodiment of the operations performed in connection with one process illustrated in FIG. 4A in accordance with one embodiment of the invention.

The functions and operations performed by test interval determinator 202 will now be described with reference to two examples illustrated in FIGS. 4A–4C, 5 and 6. FIGS. 4A–4C illustrate an exemplary process that may be performed by the present invention to determine the periodicity 208 at which electrotherapy device 100 performs a self-test 224 based on one or more characteristics of an installed power module 102. This is followed by a description of FIGS. 5 and 6 which depict an exemplary implementation of the present invention in which the current capacity of an installed battery pack 302 is used to determine whether the self-test periodicity 208 is set to one of two values provided as characteristics by battery pack 302.

FIG. 4A is a high-level flow chart of the primary operations performed by test interval determinator 202 in accordance with one embodiment of the present invention. Generally, at block 402 the periodicity of a self-test 224 is determined based on at least one characteristic 206 of installed power module 102. As noted, the characteristic(s) 206 provided by power module 102 could include the self-test periodicity. Alternatively, the self-test periodicity may be determined by test interval determinator 202 based on one or more other characteristics 206 which, in this illustrative embodiment, are also provided through power module 102. The details of this operation are described in greater detail below with reference to FIG. 4B.

Once the periodicity is determined, self-test 224 is performed repeatedly at the determined periodicity at block 404. In this general example, self-test 224 is performed at the determined periodicity indefinitely or until some undefined event occurs. The details of this operation are described in greater detail below with reference to FIG. 4C.

It should be understood that process 400 may be expanded to include multiple self-tests 224, as well as multiple installed power module 102. When more than one power module is employed, a self-test 224 may be performed at one periodicity for one installed power module and at another periodicity for another installed power module. The present invention may reconcile or consolidate the self-test periods for each of the self-tests 224 to derive an efficient, consolidated self-test protocol. Thus, the resulting self-test protocol ultimately implemented by electrotherapy device 100 may correspond to one of the protocols or may be a combination of protocols.

FIG. 4B is a flow chart of the processes performed in connection with block 402 illustrated in FIG. 4A. As noted above with reference to block 402, the periodicity of a self-test 224 is determined based on one or more characteristics 206 of installed power module 102. In accordance with one aspect of the invention, at block 406 a power module 102 having a characteristic identifier 122 is installed in electrotherapy device 100. The characteristic identifier 122 provides an indication of the periodicity at which self-test 224 is to be performed.

At block 408 self-test module 120 in electrotherapy device 100 communicates with characteristic identifier 122 to obtain the indicated self-test periodicity. This may be achieved in any number of ways, some of which having been noted above. For example, characteristics 206, stored as variables in a memory module, are retrieved by self-test module 120 through a standard data communications interface.

FIG. 4C is a flow chart of one embodiment of the operations performed at block 404 of FIG. 4A. As noted with reference to block 404, self-test 224 is performed repeatedly at the determined periodicity. At block 410 self-test module 120 of electrotherapy device 100 periodically determines whether a self-test should be performed. The time intervals with which self-test module 120 "wakes-up" to make such an inquiry may be any time interval sufficient to insure the self-test is performed at the desired periodicity.

At block 412, self-test module 120 determines when self-224 test was last performed. This may take on many forms, such as an internal timer, counter or the like, which derives its power from a separate power source or from trickle power obtained from installed power module 102. This value is then compared to the retrieved periodicity at block 414 to determine whether a self-test is to be performed now or at some later time. If self-test 224 is not to be performed, processing returns to block 410. Otherwise, self-test 224 is performed at block 416.

Figure 6:
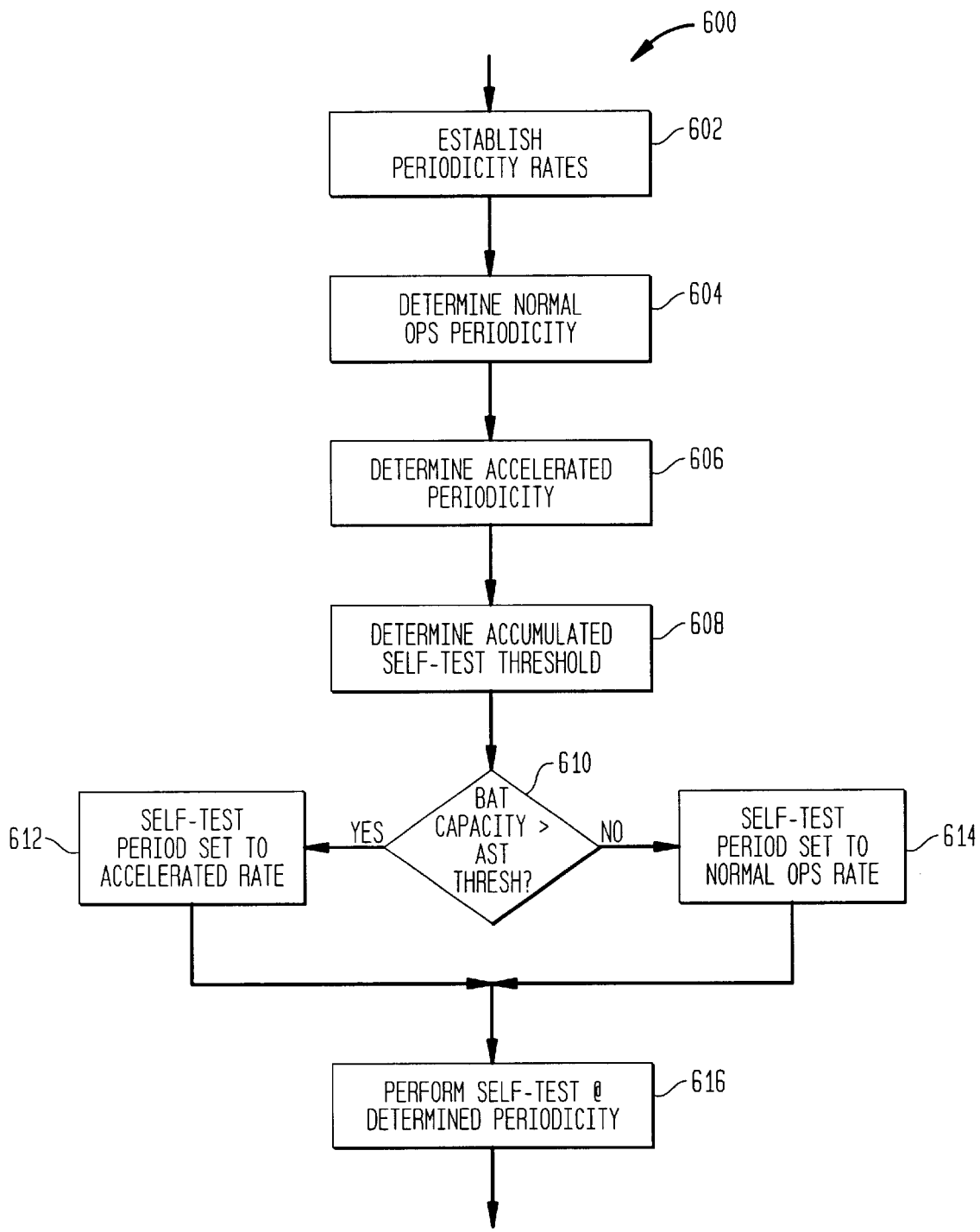
FIG. 6 is a flow chart of the operations performed by another embodiment of the present invention.

A more detailed example of how the present invention may be implemented will now be described with reference to FIGS. 5 and 6. FIG. 5 is a table illustrating the characteristics 206 stored in storage device 204 of a battery pack such as battery pack 302. FIG. 6 is a flow chart of the processes performed by self-test module 120. A self-test 224 is to be performed at a default periodicity during normal operations as determined by, for example, the capacity of the battery pack (described below). Power module 102 may also provide an additional, accelerated, self-test periodicity at which the self-test 224 is to be performed to insure power module availability. As will be appreciated, when the power module is a battery pack, additional self-tests may be performed to insure battery pack availability. Such acceleration occurs when the battery pack is near its end of life. This may be determined based on battery capacity, voltage, power delivery capability, etc. In this particular implementation, battery capacity which is used as one indication for end of life is determined based on the quantity of coulombs utilized by battery pack 302.

A common feature provided by many battery packs is an indication of when the battery pack has a low capacity. The capacity at which a "low battery" indication occurs is typically specified by the manufacturer to indicate when the battery pack has as low but not insignificant capacity suitable for providing power under normal conditions for some time. Unfortunately, there is little consistency in available power when a battery pack indicates a low battery condition, particularly with many rechargeable battery packs. This inconsistency may even occur with the same battery manufacturer, the same battery type, and even the same battery pack over time.

This inconsistency can be problematic for electrotherapy devices. Such devices, for example, portable defibrillators, must operate flawlessly to maximize likelihood of patient survival. Accordingly, it is desired to insure that the device is capable of supporting an immediate use of the device even though the device may have been last used days, weeks or months in the past.

When certain electrotherapy devices, such as rarely used defibrillators, are stored with an installed battery pack, the capacity of the battery pack depletes over time due to self-tests, consumption of trickle power or simply battery age. Ultimately, this consumes a considerable portion of the remaining energy stored in the battery pack. In this circumstance, when the defibrillator is subsequently used, the battery pack will indicate a "low battery" condition. To insure operability of the device under these operational and storage conditions, an accumulated self-test threshold battery characteristic is established in this embodiment of the invention. This threshold is set to occur prior to the manufacturer low battery condition; that is, with the consumption of a quantity of coulombs that is less than the quantity of consumed coulombs that result in a low battery condition indication. Importantly, this accumulated self-test characteristic represents a battery capacity (or other characteristic such as voltage or power delivery capability) that warrants a closer and more diligent assessment of battery pack availability. Accordingly, in one aspect of the present invention, one or more self-tests 224 are performed at an accelerated periodicity when the accumulated self-test threshold is achieved. This provides a substantially more accurate indication of battery viability and the ability of an installed battery pack to support normal operations of electrotherapy device 100. This, in turn, will promote the early replacement of rechargeable battery packs, for example, to insure reliable electrotherapy device operability upon deployment.

With this introduction, the operations performed by one embodiment of this aspect of the present invention will now be described with reference to FIGS. 5 and 6. In this exemplary implementation, characteristics 206 are represented by accessible variables stored in characteristic identifier 122. Referring now to FIG. 5, a table illustrating one format of the stored characteristic variables 206 is provided. The table illustrated in FIG. 5 includes 4 columns identifying a number of characteristics 206 represented by 3 bytes of data stored in characteristic identifier 122. The columns include a byte number 502 for reference, characteristics 206 that are stored in an associated byte 502A–502C, the possible byte values 506 and associated options/description 508 of each characteristic 206. This arrangement is for exemplary purposes only to provide an illustration of one approach to storing characteristics 206 in storage device 204. There is a myriad of formats, arrangements, etc. that may be used to store the same or other characteristics 206 in storage device 204.

Storage device 204 includes a default self-test interval characteristic 510 stored as part of byte 502A. Characteristic 510 is one characteristic 206 passed from storage device 204 to test interval determinator 202 in the embodiment illustrated in FIG. 2. In this illustrative embodiment, characteristic 510 is restricted to assuming one of four possible self-test intervals. Accordingly, byte 502A includes two bits (bits 7,6) to represent the available options 508 for default self-test interval characteristic 510. The test interval may be (1) once every 28 days (binary value 506 of 00); (2) once every 14 days (binary value 506 of 01); (3) once every 7 days (binary value 506 of 10); and (4) once every 3 days (binary value 506 of 11). In this embodiment, the default self-test interval battery characteristic 510 is the periodicity at which self-test module 120 is to perform a self test 224 during the defined normal operating conditions.

A portion of byte 502A also represents a low energy self-test interval characteristic 512. Characteristic 512 has the same format and options as default self-test interval characteristic 510, as shown in FIG. 5. Accordingly, an additional two bits (bits 5,4) of byte 502A are used to represent self-test interval characteristic 512.

A coulomb counter accumulator characteristic 516 (byte 502B) represents, for example, consumed battery capacity in units of coulombs. Coulomb counter accumulator 516 may be incremented by test interval determinator 202 based on measured or estimated power usage. For example, during runtime, accumulator characteristic 516 is incremented based on current drawn from installed battery pack 302, a relatively accurate measure of consumed battery capacity. On the other hand, when performing self-tests, internal interrupts that normally occur in electrotherapy device 100 are disabled, making it impracticable to accurately measure battery current. In such circumstances, an estimated number of coulombs may be added to coulomb counter accumulator 516 in response to the performance of each self-test. Similarly, coulomb counter accumulator 516 is estimated when electrotherapy device 100 is powered off and certain minimal components are continually powered with a trickle current.

A noted alternative embodiment is the implementation of multiple self-tests 224 each of which consume different amounts of battery capacity. In such embodiments, coulomb count accumulator 516 may be incremented a predetermined amount in response to the performance of each such self-test 224. In those embodiments in which multiple self-tests 224 are categorized according to power consumption, coulomb counter accumulator 516 may be incremented by a different amount in response to the performance of each category of self-test.

Byte 502C represents a low energy condition characteristic 518. This characteristic is the number of coulombs that, when consumed, results in a "low energy" condition. Thus, when the value in coulomb counter accumulator 516 exceeds the value of stored in low energy condition 518, installed battery pack 302 is considered to be in a low energy state.

As noted, this aspect of the invention implements an accumulated self-test characteristic representing the amount of accumulated coulombs at which accelerated self-testing is to be performed. This characteristic may be an absolute value similar to the low energy condition characteristic 518 described above. Alternatively, and as implemented in this example, this characteristic may also be a relative value. Referring to FIG. 5, an accumulated self-test delta characteristic 514 is assigned a nibble of byte 502A (bits 3–0). The accumulated self-test delta characteristic is the difference between the accumulated self-test threshold (a calculated characteristic in this embodiment) and the low energy condition threshold 518 (a sensed characteristic).

Referring to FIG. 6, the operations performed by self-test module 120 will now be described with reference to a numerical example. This example begins with two exemplary byte values for byte 502A and byte 502C (byte 502B is consumed coulombs and, therefore, is a calculated value that is incremented periodically).

Byte 502A contains byte value 506 of Hex 18 (0001 1000)

Byte 502C contains byte value 506 of Hex 96 (0101 0110)

At block 602 a coding for the self-test periodicity is established. Here, there are four possible periods at which any one of the self-tests 224 may be performed. The four periods are once every 28, 14, 7 and 3 days represented by the 2-bit binary values of 00, 01, 10 and 11, respectively. This coding scheme may be predetermined and established as a standard, or it may be specific for a particular battery type, manufacturer, etc., and may be provided to self-test module 120 as a battery characteristic 206.

At block 604 the normal operations self-test interval is determined. Test interval determinator 202 reads bits 6,7 of byte 502A, which represent default self-test interval characteristic 510. In the above example wherein byte 502A has a value 506 of (0001 1000), bits 7,6 contain the binary value of (00). Using the noted coding scheme, the binary value (00) represents a normal self-test interval of once every 28 days.

Similarly, at block 606 the low energy self-test interval characteristic 512 is determined. The low energy self-test interval may be determined based on the capacity, voltage, power delivery capability, etc. Test interval determinator 202 reads bits 5,4 of byte 502A. In the above example wherein byte 502A has a value 506 of (0001 1000), bits 5,4 contain the binary value of (01). Using the noted coding scheme, the binary value (01) represents a low energy self-test interval 512 of once every 14 days. Thus, the periodicity of the self-test is to be accelerated from once every 28 days to once every 14 days when, for example, the capacity of installed battery pack 102 reaches the accumulated self-test.

Accumulated self-test threshold characteristic is determined at block 608. One method for determining the accumulated self-test threshold is to subtract the accumulated self-test delta characteristic 514 from low energy condition characteristic 518.

First, accumulated self-test delta characteristic 514 is read and converted to coulombs. As noted, the accumulated self-test delta characteristic 514 is stored in bits 0–3 of byte 502A. In the above example wherein byte 502A contains byte value 506 of Hex 18 (0001 1000), the accumulated self-test delta characteristic 514 has a value of 8 (binary 1000). As noted in FIG. 5, the least significant bit (LSB) for this variable is 128 coulombs. Thus, the accumulated self-test delta characteristic 514 has a value of 1024 coulombs (8*128=1024).

Low energy condition characteristic 518 is also read and converted to coulombs. As noted, low energy condition characteristic 518 is stored in byte 502C. In the above example wherein byte 502C contains byte value 506 of Hex 96 (0101 0110), low energy condition characteristic 518 has a value of 86 (binary 01010110=decimal 86). The LSB for this characteristic is also 128 coulombs. Thus, the low energy condition is 11,008 coulombs (86*128=11008).

Since the accumulated self-test delta characteristic 514 value is the difference between low energy condition characteristic 518 and the accumulated self-test threshold characteristic, subtracting the accumulated self-test delta characteristic 514 from the low energy condition threshold characteristic 518 yields the accumulated self-test threshold characteristic. That is, the accumulated self-test threshold is set to the low battery condition (11008) less the accumulated self-test delta (1024), or 9984 coulombs (11008−1024= 9984). Thus, the accumulated self-test threshold occurs when 9,984 coulombs are consumed while the low energy condition threshold occurs subsequently when 11,008 coulombs are consumed. It should be understood that the accumulated self-test threshold might be set as a percentage based on a low battery condition or any other means.

At block 460 current coulomb counter accumulator 516 is converted and compared to the determined accumulated self-test threshold. In this example, when less than 9,984 coulombs are consumed, processing advances from decision block 458 to block 464 at which point self-test module 120 performs self-test 224 at a periodicity for normal operations; that is once every 28 days. Once 9,984 coulombs have been consumed, processing advances from decision block 460 to block 462 at which point self-test module 120 performs self-test 224 at an accelerated rate as specified in low energy self test interval; that is, once every 14 days. This is implemented at block 466.

It should be understood that in other embodiments, characteristics such as power module type (use model, training model, manufacturing model), battery chemistry, rechargeability and the like may be considered by test interval determinator 202 in determining the self-test interval, the conditions under which the self-test interval changes, etc. The results of these calculations may be stored in installed power module 102 for informing future electrotherapy devices that receive the power module.

In one aspect, the present invention is configured to be installed in any portable defibrillator. Here, self-test module 120 determines the periodicity of a full charge/discharge self-test 224 based on the battery characteristics of capacity and rechargeability to provide a self-test protocol that is correlated to the capacity of installed battery pack 102 and the use model of the defibrillator. Of course, the self-test protocol could be correlated to, for example, voltage.

Portable defibrillators that are used by emergency medical service (EMS) and other first responders may be operated a few times a week. Defibrillators having such a high use model are generally equipped to receive a rechargeable battery pack. More advanced defibrillators such as AEDs are installed in public facilities such as commercial aircraft, stadiums and the like. These defibrillators have a relatively low use model and are likely to be used infrequently as compared to the above-noted counterparts, perhaps once or twice per year. Such defibrillators are generally equipped to receive a non-rechargeable battery pack, which are best suited for such use models.

In one embodiment, a greater self-test periodicity is implemented when installed battery pack 102 is a rechargeable battery pack than when it is a non-rechargeable battery pack. Since rechargeable battery packs are conventionally installed in frequently operated defibrillators (relatively high use model) while non-rechargeable battery packs are installed in infrequently operated defibrillators (relatively low use model), this approach provides a self-test protocol that is correlated with the use model of the device. Further, a relatively high self-test periodicity provides a more accurate assessment of a frequently used rechargeable battery pack while a relatively low periodicity avoids unnecessarily consuming the capacity of an infrequently used non-rechargeable battery pack.

In one embodiment, the battery characteristic of rechargeability is derived from battery chemistry since only certain battery chemistries are rechargeable. Similarly, the anticipated use model of the defibrillator may also be derived from battery chemistry since non-rechargeable battery packs are conventionally installed in less frequently used portable defibrillators while rechargeable battery packs are installed in defibrillators that are used relatively often.

In addition, the periodicity of each such self-test may also be adjusted based on, for example, current battery capacity. For example, the self-tests may be performed as infrequently as practical when the battery capacity is high to insure system reliability while maximizing battery life. As battery capacity decreases, the full charge/discharge self-test is performed more often. One example of such an approach is described above with reference to FIG. 6. This will improve confidence in the installed rechargeable battery which, as noted, becomes inconsistent as capacity decreases.

It should be understood that various changes and modifications of the embodiments shown in the drawings and described in the specification may be made within the spirit and scope of the present invention. For example, although in the embodiments of the invention described herein the battery characteristics are provided by the installed battery pack(s), the invention is not limited to such embodiments. Rather, the invention contemplates that such information may be provided elsewhere including, for example, from the self-test module 120 itself, through an operator control input, etc. Given this, it is a preferred approach to implement the battery characteristic identifier as disclosed herein because it provides the greatest design flexibility. Each power module provides characteristics specifically related to its capabilities, which may change over time, whether it be for specific power modules or types of power modules, advances in battery technology that result in the introduction of new or different power modules, etc. Self-test module 120 on the other hand, can then remain consistent over time, performing one or more self-tests with a periodicity that is set in response to the characteristics provided by the installed power modules. Thus, implementation of self-test module 120 results in an electrotherapy device 100 that need not be restricted to a particular type of power module. Instead, electrotherapy device 100 may receive different types of power modules each providing the information necessary for self-test module 120 to determine the appropriate self-test protocol to implement for that power module. Also, as noted, the present invention may be implemented with any type of power module. In the disclosed aspects of the invention, the implemented power module is a battery pack. Accordingly, the characteristics considered by test interval determinator 202 include battery-specific characteristics. In alternative aspects of the invention, an AC power pack is implemented. In such implementations, the type of characteristics considered by test interval determinator 202 could be those related to the ability of the AC power pack to support electrotherapy device 100 in its intended use model. For example, availability of DC power, voltage levels, temperature and other characteristics of an AC power pack may be considered in determining the periodicity of one or more self-tests 224. Thus, the present invention is not limited to any system, technique, data format or protocol, architecture, storage or communication device for the battery characteristics or the derived self-test periodicity. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A method for performing automatically a self-test in a powered device, the method comprising the steps of:
    (a) determining a periodicity at which the self-test is to be performed based on one or more characteristics of an installed power module; and
    (b) performing the self-test at the determined periodicity.

2. The method of claim 1, further comprising the step of:
    (c) prior to step (a), storing one or more variables in a storage device of the power module, wherein the variables are indicative of the characteristics of the power module considered in step (a).

3. The method of claim 1, wherein the determining step further comprises the steps of:
    (a)(i) monitoring the characteristics available from the installed power module; and
    (a)(ii) determining the periodicity for the self-test, wherein the periodicity is based on at least one of the monitored characteristics.

4. The method of claim 1, wherein the performing step further comprises the steps of:
    (b)(i) retrieving the periodicity for the self-test from a memory device included in the installed power module; and
    (b)(ii) performing the self-test at a corresponding retrieved periodicity.

5. The method of claim 1, wherein the powered device is a medical device.

6. The method of claim 5, wherein the medical device is a defibrillator.

7. The method of claim 1, wherein the power module is a battery pack, and wherein the characteristics of the installed battery pack are selected from the group comprising battery chemistry, rechargeability, current battery capacity, self-test periodicity and projected frequency of use.

8. A test interval determinator for determining a periodicity at which a periodic automatic self-test of a powered device is to be performed, wherein the determinator is configured to receive at least one characteristic of a power module installed in the device, and to generate a period at which the self-test is to be performed, wherein the self-test period is a function of the received power module characteristics.

9. The test interval determinator of claim 8, wherein the power module is selected from the group comprising a rechargeable battery pack, a non-rechargeable battery pack and an AC power module.

10. An electrotherapy device that performs one or more periodic automatic self-tests, wherein each self-test is performed at a periodicity that is a function of one or more characteristics of an installed power module.

11. A system for determining a periodicity at which power-consuming self-tests are performed in a powered device, the system comprising:

a battery pack comprising an indicator of one or more characteristics of the battery pack; and
    a self-test module constructed and arranged to perform one or more automatic self-tests, the automatic self-tests performed with a periodicity that is based on the indicated battery characteristics.

12. The system of claim 11, wherein the system is implemented in a medical device.

13. The system of claim 12, wherein the medical device is a defibrillator.

14. The system of claim 11, wherein the battery characteristics are selected from the group comprising battery chemistry, rechargeability, current battery capacity, self-test periodicity and projected frequency of use.

15. The system of claim 12, wherein the indicator of the battery characteristics comprises:
    a memory module integrated in the battery pack, the memory module having stored therein one or more variables individually or collectively representative of the indicated battery characteristics.

16. The system of claim 11, wherein the battery characteristics are indicative of the ability of the installed battery pack to support the operations of the device.

17. A system for determining a periodicity at which power-consuming self-tests are performed in a powered device, the system comprising:
    a power module comprising an indicator of one or more characteristics of the power module; and
    a self-test module constructed and arranged to perform one or more automatic self-tests, the automatic self-tests performed with a periodicity that is based on the indicated power module characteristics.

18. The system of claim 17, wherein the system is implemented in a medical device.

19. The system of claim 18, wherein the medical device is a defibrillator.

20. The system of claim 17, wherein the power module characteristics are selected from the group comprising battery chemistry, rechargeability, current battery capacity, self-test periodicity and projected frequency of use.

21. The system of claim 18, wherein the indicator of the battery characteristics comprises:
    a memory module integrated in the power module, the memory module having stored therein one or more variables individually or collectively representative of the indicated power module characteristics.

22. The system of claim 17, wherein the power module characteristics are indicative of the ability of the installed power module to support the operations of the device.

23. A power module for installation in a powered device that performs automatic self-tests, comprising:
    an apparatus constructed and arranged to provide the device with an indication of one or more characteristics of the power module for use in determining the periodicity of each self-test.

24. The power module of claim 23, wherein the apparatus comprises:
    a memory device suitable for storing digital values representing the indicated characteristics.

25. The power module of claim 23, wherein the apparatus comprises:

circuitry accessible by the device, wherein the circuitry is configured to have detectable electrical characteristics that represent the indicated characteristics.

26. The power module of claim 23, wherein the power module is selected from the group comprising a rechargeable battery pack, a non-rechargeable battery pack and an AC power module.

27. A defibrillator that performs a self-test at a periodicity based on a use model of the defibrillator, wherein the use model is derived from an installed power module.

28. The defibrillator of claim 27, wherein the use model is derived from one or more of the group comprising power module identification, battery chemistry, capacity, voltage, power delivery capability and energy.

* * * * *